US00PP10296P

United States Patent [19]

Whitcomb

[11] Patent Number: Plant 10,296

[45] Date of Patent: Mar. 24, 1998

[54] CRAPE MYRTLE SHRUB NAMED 'WHIT II'

[76] Inventor: Carl E. Whitcomb, P.O. Box 2383, Stillwater, Okla. 74076

[21] Appl. No.: 732,773

[22] Filed: Oct. 15, 1996

[51] Int. Cl.[6] ..... A01H 5/00

[52] U.S. Cl. ..... Plt./67.3

[58] Field of Search ..... Plt./67.3

[56] References Cited

U.S. PATENT DOCUMENTS

| | | | |
|---|---|---|---|
| P.P. 4,182 | 1/1978 | Chopin | Plt./54 |
| P.P. 4,183 | 1/1978 | Chopin | Plt./54 |
| P.P. 4,184 | 1/1978 | Chopin | Plt./54 |
| P.P. 4,185 | 1/1978 | Chopin | Plt./54 |
| P.P. 5,302 | 10/1984 | Chopin | Plt./54 |
| P.P. 6,365 | 11/1988 | Chopin | Plt./54 |

*Primary Examiner*—James R. Feyrer
*Assistant Examiner*—Elizabeth C. Kemmerer
*Attorney, Agent, or Firm*—Bill D. McCarthy; Phillip L. Free, Jr.; Randall K. McCarthy

[57] ABSTRACT

A new and distinct variety of crape myrtle, *Lagerstroemia indica*, which is characterized by a vigorous, upright growth habit, leathery leaves which emerge crimson and quickly change to medium green, few seed heads, moderate seed head production, inflorescences which are eight to fourteen inches tall and six to ten inches wide, flower buds that are crimson before opening, and cherry red flower petals with occasional slight white variegation.

2 Drawing Sheets

BACKGROUND OF THE INVENTION

1. Field of the Invention

The present invention relates to a new and distinct variety of cultivar of the ornamental shrub, *Lagerstroemia indica*, commonly known as crape myrtle.

2. Description of the Prior Art

The crape myrtle shrub is native to eastern China and was introduced into North America in the late 1700s. Since then this popular ornamental shrub has been grown extensively throughout the continent. Over the years, seedlings and hybrids between *L. indicia* and *L. fauriei*, have been selected for various growth forms, flower colors, or other features and propagated asexually. An assortment of methods have been utilized in attempting to develop improved varieties of crape myrtles, at least several of which have had U.S. Plant Patents issued.

For example, U.S. Plant Pat. No. 4,182, U.S. Plant Pat. No. 2,183, U.S. Plant Pat. No. 4,184 and U.S. Plant Pat. No. 4,185 disclose and claim a series of four new varieties of *Lagerstroemia indica* produced by crossing previously known varieties. Each of these new varieties was characterized as having a weeping growth habit at maturity. U.S. Plant Pat. No. 5,302 also discloses a new variety of crape myrtle exhibiting a weeping growth habit at maturity. U.S. Plant Pat. No. 365 discloses a variety of crape myrtle derived from seedlings that had been treated with a mutation inducing chemical. The plant was characterized as having variegated pink flowers bordered by pure white and flowering over an extremely long period of time.

It is generally known that ethyl methane sulfonic acid methyl ester, EMS, is capable of producing plant mutations. EMS sometimes induces partial or complete sterility in the mutant plant and the mutants often have thicker than normal leaves and variegated flowers, with an occasional flower that is a solid color among the predominantly variegated flowers. The new variety of crape myrtle of the present may be such a mutant.

SUMMARY OF THE INVENTION

The present invention involves the discovery of a new and distinct variety of crape myrtle, *Lagerstroemia indica*, which is characterized by a vigorous, upright growth habit, large shrub or small tree that may reach 20 feet in height. The leaves of the plant emerge crimson and quickly change to medium green and are more leathery than the species average. Inflorescences are eight to 14 inches tall and six to 10 inches wide. Flower buds are crimson before opening. Individual petals are cherry red. Occasionally a flower will have a slight, white variegation. Old flowers fall from the inflorescence with little discoloration. Flowering generally begins in July in north central Oklahoma, and flowering continues until frost. Seed head production is moderate which further enhances the prolonged flowering.

BRIEF DESCRIPTION OF THE DRAWINGS

FIG. 1 is a photographic view in full color of the flowering of the new crape myrtle shrub.

FIG. 2 is a photographic view in full color of the crimson flower bud and cherry red flower of the shrub of FIG. 1.

FIG. 3 is a photographic view in full color of the leathery, medium green, mature foliage of the shrub of FIG. 1.

DESCRIPTION OF THE VARIETY

The new variety of crape myrtle, which has been the cultivar name "Whit II," was selected from about 2000 seedlings grown from a seedling parent that had been selected because of the upright growth, dark foliage, and near red flowers and because the parent produced seeds with good germination and seedling vigor. Prior to planting the seeds were treated with ethyl methane sulfonic acid methyl ester, EMS, which is generally known to be capable of producing plant mutations. Treated seeds were planted in small flats in the greenhouse. After the seeds germinated, the seedlings were transplanted into small containers and mildew was introduced from susceptible seedlings in small containers. Seedlings susceptible to mildew or with poor vigor were rogued out and the remainder of the seedlings were planted in rows in an open field for further evaluation. The new variety was selected from the population in the field for the unique flower color, vigorous upright growth and dense, leathery foliage. It is probably a mutant arising from the EMS treatment. EMS is known to induce sterility. Mutant plants resulting from EMS treatments often have thicker than normal leaves with variegated flowers with an occasional flower that is solid color among the predominantly variegated flowers. Such characteristics have been observed in this new variety of crape myrtle, although, the flower variegation is slight and only occasionally expressed.

Softwood cuttings taken from the original parent have been successfully rooted in a media of peat and perlite under intermittent mist in Oklahoma. Subsequent cuttings taken from plants resulting from previous cuttings have been similarly rooted. Growth, flowering, and flower and foliage color remain consistent with the parent. The plant does not reproduce from seed.

A detailed description of the new variety of crape myrtle follows:

Parentage: Selected from over 2000 crape myrtle seedlings grown from a selected seedling parent. The seeds were treated with EMS to induce mutations. The thick leathery leaves, variegated flowers, long bloom time, and partial sterility are indications that the new variety is a mutant.

Growth: The plant is a vigorous upright grower when young. The selected plant reached a height of seven feet in three years in the field with minimum care. Height with age may reach 20 feet or more. Vegetative growth is rapid in spring and continues until summer when flowering begins. Only modest growth occurs after flowering begins. Unlike most crape myrtle varieties which produce many vertical stems with moderate side branches, this new crape myrtle produces a vigorous growing central stem with moderate side branches, thus creating an upright tree form. If the central stem is cut or killed then a proliferation of upright stems result.

Foliage: Leaves are similar in size to the species average, but are more thick and leathery and with excellent retention. New leaves emerge crimson, Grayed-purple Group 185-A and CIE coordinates. 0.519, 0.312, 8.5 (color notations from The Royal Horticulture Society Colour Chart, 1966 and the Commission International de l'Eclairage 1931) and quickly change to medium green (FIG. 3), Green Group 137-A (RHS) and CIE 0.325, 0.419, 10.0. The color varies with light intensity and growing conditions. Foliage has been very resistant to powdery mildew.

Flowers: Individual petals are cherry red (FIG. 2), Red Group 46-C (RHS) and CIE 0.541, 0.319, 16.3. The presence of a slight white margin is only occasionally expressed and varies with temperature, light intensity and growing conditions, but is generally absent. As the flowers age they generally fall cleanly from the inflorescence without discoloring and becoming unattractive. Unopened flower buds are crimson, Red Group 46B (RHS) and CIE 0.575, 0.324, 11.8. Inflorescences are eight to 14 inches tall and six to 10 inches wide (FIG. 1). The new variety begins flowering in July and continues into October. This period is longer than most seedlings and cultivars of crape myrtle. Flower continues during drought and periods of prolonged heat. Seed set is moderate which contributes to the extended flowering.

Cold hardiness: The new variety of crape myrtle has withstood temperatures of −5° F., −2° F. and 0° F. with no injury. The top of the plant was killed to the soil line at −13° F., but quickly regrew the following spring and flowered in summer.

I claim:

1. A new and distinct variety of *Lagerstroemia indica*, crape myrtle, plant substantially as shown and described and partially characterized by a vigorous upright, growth habit large shrub or small tree that may reach 20 feet or more in height, crimson new leathery foliage that quickly changes to medium green, crimson flower buds, cherry red flowers in large inflorescences, moderate seed production and a long bloom period.

* * * * *

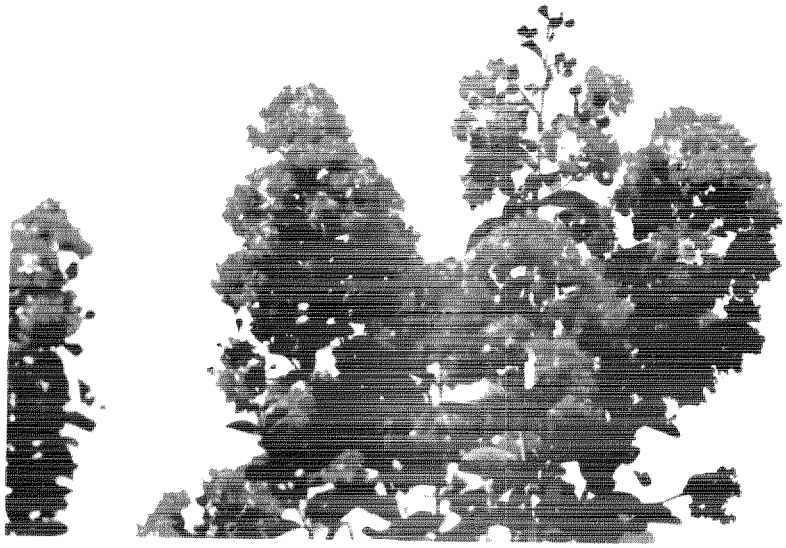
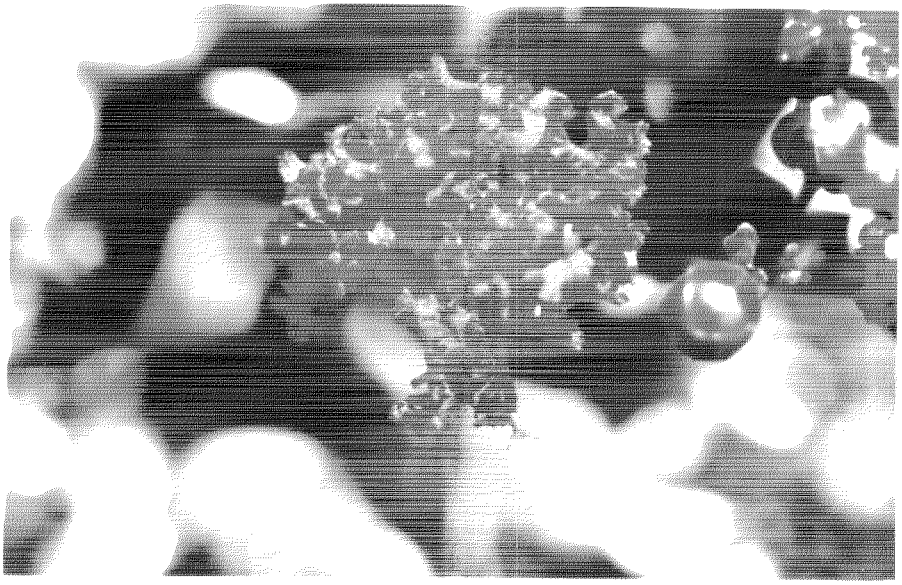

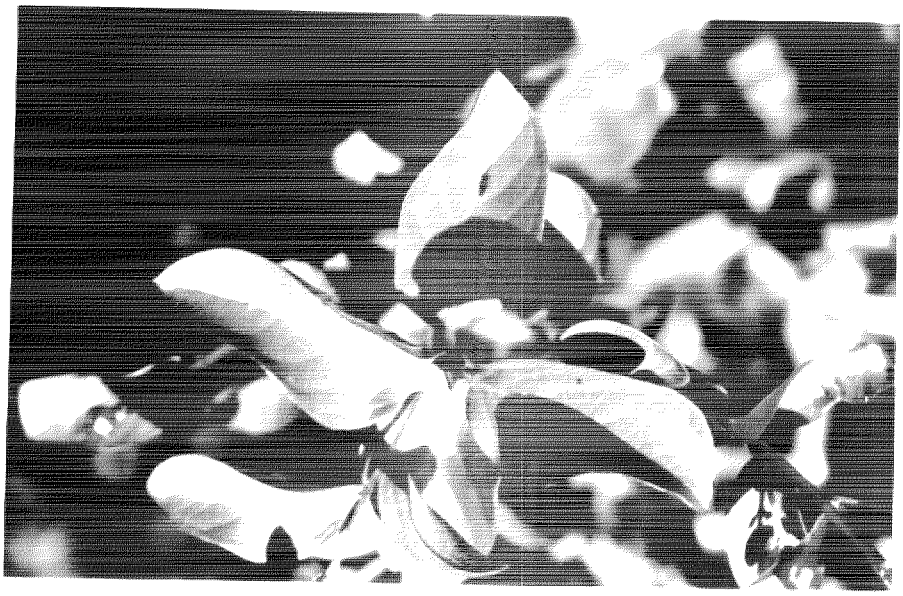

UNITED STATES PATENT AND TRADEMARK OFFICE

CERTIFICATE OF CORRECTION

PATENT NO. : PP 10,296
DATED : March 24, 1998
INVENTOR(S) : Carl E. Whitcomb

It is certified that error appears in the above-identified patent and that said Letters Patent is hereby corrected as shown below:

Column 1,
Line 19, replace "2,183" with -- 4,183 --.
Line 25, replace "365" with -- 6,365 --.

Signed and Sealed this

Nineteenth Day of March, 2002

*Attest:*

*Attesting Officer*

JAMES E. ROGAN
*Director of the United States Patent and Trademark Office*